(12) United States Patent
Yao et al.

(10) Patent No.: US 10,851,129 B2
(45) Date of Patent: Dec. 1, 2020

(54) COMPOSITION, CROCINS ACTIVE SITE, AND USES THEREOF

(71) Applicant: Jinan University, Guangzhou, Guangdong (CN)

(72) Inventors: Xinsheng Yao, Guangdong (CN); Dan Zhang, Beijing (CN); Yang Yu, Guangdong (CN); Xiuqi Bao, Beijing (CN); Yang Ni, Guangdong (CN); Caixia Zang, Beijing (CN)

(73) Assignee: Jinan University, Guangdong (CN)

( * ) Notice: Subject to any disclaimer, the term of this patent is extended or adjusted under 35 U.S.C. 154(b) by 131 days.

(21) Appl. No.: 16/097,247

(22) PCT Filed: Mar. 16, 2017

(86) PCT No.: PCT/CN2017/076910
§ 371 (c)(1),
(2) Date: Oct. 27, 2018

(87) PCT Pub. No.: WO2017/185899
PCT Pub. Date: Nov. 2, 2017

(65) Prior Publication Data
US 2019/0112326 A1    Apr. 18, 2019

(30) Foreign Application Priority Data
Apr. 29, 2016  (CN) .......................... 2016 1 0284549

(51) Int. Cl.
*A61K 31/7016* (2006.01)
*C07H 13/06* (2006.01)
(Continued)

(52) U.S. Cl.
CPC ............ *C07H 13/06* (2013.01); *A23L 33/105* (2016.08); *A61K 31/7024* (2013.01);
(Continued)

(58) Field of Classification Search
CPC combination set(s) only.
See application file for complete search history.

(56) References Cited

U.S. PATENT DOCUMENTS

2014/0141082 A1* 5/2014 Gao ...................... A61K 31/353
424/474

FOREIGN PATENT DOCUMENTS

| CN | 1347868 A | 5/2002 |
| CN | 101012248 A | 8/2007 |

(Continued)

OTHER PUBLICATIONS

Debnath et al. ("Antioxidant activity of Gardenia jasnninoides Ellis fruit extracts," Food Chemistry 128:697-703, 2011,.*
(Continued)

*Primary Examiner* — Rosanne Kosson
(74) *Attorney, Agent, or Firm* — Suzannah K. Sundby, Esq.; Canady + Lortz LLP

(57) ABSTRACT

A composition, and a crocins active site extracted from *Gardenia jasminoides* Ellis, mainly comprising the following ingredients: crocetin di-β-D-gentiobioside, crocetin-β-D-glucopyranosyl-β-D-gentiobioside, crocetin di-β-D-glucopyranoside, 13Z-crocetin di-β-D-gentiobioside, neocrocin B, crocetin mono-β-D-gentiobioside, 13Z-crocetin-8-O-β-D-gentiobioside, 13Z-crocetin-8'-O-β-D-gentiobioside, and crocetin mono-β-D-glucopyranoside. Pharmacological experiment results show that the crocins active site can effectively improve learning and memory injuries in mice induced by scopolamine and amyloid β protein.

4 Claims, 6 Drawing Sheets

(51) Int. Cl.
*A61K 31/7024* (2006.01)
*A61K 36/744* (2006.01)
*A23L 33/105* (2016.01)
*C07H 13/04* (2006.01)
*A61P 25/28* (2006.01)

(52) U.S. Cl.
CPC ............ *A61K 36/744* (2013.01); *A61P 25/28* (2018.01); *C07H 13/04* (2013.01); *A61K 2236/00* (2013.01); *A61K 2236/15* (2013.01); *A61K 2236/331* (2013.01); *A61K 2236/333* (2013.01); *A61K 2236/51* (2013.01); *A61K 2236/53* (2013.01)

(56) References Cited

FOREIGN PATENT DOCUMENTS

| | | |
|---|---|---|
| CN | 102432455 A | 5/2012 |
| CN | 102516325 A | 6/2012 |
| CN | 103387489 A | 11/2013 |
| CN | 105935363 A | 9/2016 |

OTHER PUBLICATIONS

International Search Report received in PCT/CN2017/076910 dated Jun. 1, 2017.
Written Opinion received in PCT/CN2017/076910 dated Jun. 1, 2017.
Notification to Grant Patent Right for Invention received in CN201610284549 dated Jan. 19, 2017.
First Office Action received in CN201610284549 dated Nov. 10, 2016.

* cited by examiner compared with control group, ###P<0.001; compared with model group, P<0.01, *P<0.001 compared with control group, #P<0.05; compared with model group, *P<0.05

COMPOSITION, CROCINS ACTIVE SITE, AND USES THEREOF

TECHNICAL FIELD

The present disclosure relates to a composition and to a Chinese herbal extract, specifically relates to a crocins active site extracted from *Gardenia jasminoides* Ellis and use thereof in preventing and treating diseases, such as Alzheimer's disease, and more specifically relates to a *Gardenia* sourced crocins active site and the application of the active ingredients contained therein to preparation of medicines or health care products for preventing and treating of senile dementia associated diseases like Alzheimer's disease.

BACKGROUND ART

Crocin is a water-soluble carotenoid with a particular structure and includes crocetin and sugar esters formed by the combination of it with different saccharide groups. It is a pigment shared by saffron and *Gardenia*. Due to its good water solubility, crocin is widely used in liquors, dishes, cakes and pastries as a colorant. Several studies show that crude saffron extracts, *Gardenia* yellow pigment and monomer ingredients e.g. crocin and crocetin, etc. exhibit highly efficient and low toxic pharmacological activity in, for example, protecting central nervous system[1-4], protecting cardio-cerebral vascular system[5-6] and antagonizing malignant tumors[7-9].

Saffron originates in southern Europe, Mediterranean and Iran, etc. Iran produces 95% of saffron in the world. Saffron is cultivated in Zhejiang, Jiangsu, Shandong and Beijing, etc. in China in a small amount. The stigma of saffron is used as medicine, which yield is extremely low (less than 1 kg/mu (1 mu=666.6666667 $m^2$)) and is very expensive (2000 dollars/kg). Therefore, it is known as "gold in plants". The increasing medical and edible demands for crocins ingredients make it significant to search for and discover other plants rich of crocins ingredients.

*Gardenia jasminoides* Ellis, also known as *Gardenia* and cape jasmine, etc., which is a type of plant under the genus *Gardenia* Ellis of rubiaceae, is widespread throughout central and southern provinces in China. *Gardenia* is first recorded in *Sheng Nong's Herbal Classic*. It is also found in pharmacopoeias and *Compendium of Materia Medica* from ancient China. It is among the first medicinal-edible resources issued by the Ministry of Health. Taken orally, *Gardenia* descends fire, relieves restlessness, clear heat, promotes urination, cools blood and leaches internal heat. Applied externally, it cures sprain and bruise. Industrially, it is a good resource for extracting natural pigment. Modern chemical and pharmacological researches found that *Gardenia* contains chemical ingredients like iridoid, crocin, triterpene, flavone and quinic acid. Iridoids and crocins are representative ones[10-11]. Pharmacologically, *Gardenia* is mainly anti-inflammatory, antalgic, cholagogic, hepatoprotective, antioxidant and antineoplastic[10-11].

As a commonly used Chinese herbal medicine, *Gardenia* is widely planted and distributed, highly yielded (up to 200 kg/mu of dry *Gardenia* fruit, 5000 tons/year in China) and reasonably priced (sold for 15 yuan/kg). It contains a relatively high content of crocins ingredients, which are also rich in types. Therefore, *Gardenia* can be expected to be a desired plant for extracting crocins in addition to saffron.

Alzheimer's Disease (AD) is a progressive neurodegenerative disease related with ageing and featured by amnesia, cognitive disorder and personality change. AD is the most common type of senile dementia. Patients suffered from AD first present a symptom of amnesia, and develop to decrease in orientation, comprehension, judgment and memory. Patients in the advanced stage decline in all aspects. They lose their intelligence, have increasingly obvious movement and speech disorder, lie on bed all day long and cannot take care of themselves. In the end, most of them die of secondary infection and failure[11].

Along with the ageing in the world, the incidence rate of AD is increasing rapidly every year, bringing heavy economic and family burdens to the societies and people in all countries, especially in developing ones. First described by a German doctor Alzheimer in 1906, for over 100 years, AD remains an irreversible disease. It is internationally recognized that there is no method or medicine which can cure such disease. As can be seen, without desirable therapeutic drug, the screening, research & development of anti-senile dementia drugs have quite a market prospect and profound social significance.

By the way, a patent document CN104491075A reports a method of extracting crocin enriched site from *Gardenia* applying the combination of macroporous resin column and sephadex column and proves its therapeutic effect in depression treatment through stress induced depression experiment. However, the focus of the patent document is on 50% ethanol site and the process of applying the combination of macroporous resin column and sephadex column is complicated. In addition, the patent document does not specify the composition and content of the crocin enriched site. And the effective dosage in the example is high (100-400 mg), which is possibly caused by a low purity of the crocin enriched site therein.

REFERENCES

[1] Karakani A.-M., Riazi G., Mahmood G.-S., et al. Inhibitory effect of corcin on aggregation of 1N/4R human tau protein in vitro[J]. *Iranian journal of basic medical sciences*. 2015, 18(5), 485-92.

[2] Papandreou M.-A., Kanakis C.-D., Polissiou M.-G., et al. Inhibitory Activity on Amyloid-β Aggregation and Antioxidant Properties of *Crocus sativus* Stigmas Extract and Its Crocin Constituents [J]. *Journal of Agriculture and Food Chemistry*. 2006, 54(23), 8762-8768.

[3] Akhondzadeh S., Sabet M.-S., Harirchian M.-H., et al. A 22-week, multicenter, randomized, double-blind controlled trial of *Crocus sativus* in the treatment of mild-to-moderate Alzheimer's disease [J]. *Psychopharmacology*. 2010, 207(4), 637-643.

[4] Farokhnia M., Shafiee S.-M., Iranpour N., et al. Comparing the efficacy and safety of *Crocus sativus* L. With memantine in patients with moderate to severe Alzheimer's disease: a double-blind randomized clinical trial [J]. *Human Psychopharmacology*. 2014, 29(4), 351-359.

[5] Zheng Y.-Q., Liu J.-X., Wang J.-N., et al. Effects of crocin on reperfusion-induced oxidative_nitrative injury to cerebral microvessels after global cerebral ischemia [J]. *Brain Research.* 2007, 1138, 86-94.

[6] Higashino S., Sasaki Y., Giddings J.-C., et al. Crocetin, a Carotenoid from *Gardenia jasminoides* Ellis, Protects against Hypertension and Cerebral Thrombogenesis in Stroke-prone Spontaneously Hypertensive Rats [J]. *Phytotherapy Research.* 2014, 28(9), 1315-1319.

[7] Shengyu Dong, Fumei Liu, Xiangyong Li, Inhibiting Effect of Crocin on Proliferation and Migration of CNE2 Cells [J]. *Journal of Hubei University for Nationalities (Medical Edition).* 2013, 30(2), 6-12.

[8] Xinxing Wang, Zhenghong Yu, Shulu Shi, et al. Studies on the Inhibiting Effect and Mechanism of Crocin on the Proliferation of Human Lung Adenocarcinoma SPC-A1 Cells [J]. *Chinese Clinical Oncology.* 2013, 18(4), 295-299.

[9] Fuxiong Chen, Jia Tao, Sui Huang, et al. Clinical Research and Virus Infection Features of EB Virus Infection in Children Associated IM and EBV-AHS [A]. *Chinese Pediatric Society, Chinese Medical Association. Proceedings of 17th National Pediatric Academic Conference of Chinese Medical Association (First Volume)* [C]. Chinese Pediatric Society, Chinese Medical Association. 2012:1.

[10] Xiangle Meng, Hongwei Li, Yan Li, et al. Research on the Chemical Ingredients of *Gardenia* and the Pharmacological Effects thereof [J]. *Chinese Journal of New Drugs.* 2011, 20(11), 959-967.

[11] Yang Yu, Study on Anti-Senile Dementia Active Ingredients in *Gardenia* [D]. Shenyang Pharmaceutical University, 2010.

[12] Calsteren M.-R.-V., Bissonnette M. C., Cormier F., et al. Spectroscopic Characterization of Crocetin Derivatives from *Crocus sativus* and *Gardenia* jasminoides[J]. *Journal of Agriculture and Food Chemistry.* 1997, 45 (4), 1055-1061.

[13] Haibo Li, Yang Yu, Zhenzhong Wang, et al. Study on the Chemical Ingredients of Reduning Injection (II) (J). *Chinese Herbal Medicines.* 2015, 46(11), 1597-1602.

[14] Hong Chen, Yongqing Xiao, Li Li, et al. Study on the Chemical Ingredients of *Gardenia* [J]. *China Journal of Chinese Materia Medica.* 2007, 32(11), 1041-1043.

SUMMARY

In view of the above problems in the prior art, a purpose of the present disclosure is to provide a composition which includes several newly structured crocins compounds.

Another purpose of the present disclosure is to provide a crocins active site extracted from *Gardenia* with explicit ingredients and content and its application to preparing drugs, food or food additives for preventing and treating dementia associated diseases like Alzheimer's disease.

A further purpose of the present disclosure is to provide a composition including *Gardenia* sourced crocins active site, a traditional Chinese medicine, a natural product and a drug with central nervous system protection effect, and its application to preparing drugs or health care products for preventing and treating senile dementia associated diseases like Alzheimer's disease.

To achieve the above purposes, the following technical solutions are employed in the present disclosure.

[1] A composition, wherein the composition includes neocrocin B (5) and crocetin di-β-D-gentiobioside (1).

[2] The composition according to item [1], wherein it further includes crocetin mono-β-D-gentiobioside (6).

[3] The composition according to item [1], wherein it further includes 13Z-crocetin di-β-D-gentiobioside (4).

[4] The composition according to item [1], wherein it further includes crocetin-β-D-glucopyranosyl-β-D-gentiobioside (2).

[5] The composition according to item [1], wherein it further includes crocetin-β-D-glucopyranosyl-β-D-gentiobioside (2), crocetin di-β-D-glucopyranoside (3), 13Z-crocetin di-β-D-gentiobioside (4), crocetin mono-β-D-gentiobioside (6), 13Z-crocetin-8-O-β-D-gentiobioside (7), 13Z-crocetin-8'-O-β-D-gentiobioside (8) and crocetin mono-β-D-glucopyranoside (9).

[6] The composition according to item [5], wherein the composition has following respective content of each ingredient:

crocetin di-β-D-gentiobioside (1) 8.0%-12.0% crocetin-β-D-glucopyranosyl-β-D-gentiobioside (2) 3.5%-5.5% crocetin di-β-D-glucopyranoside (3) 0.5%-2.5%

13Z-crocetin di-β-D-gentiobioside (4) 6.0%-8.0% neocrocin B (5) 5.5%-7.5% crocetin mono-β-D-gentiobioside (6) 40.0%-50.0%

13Z-crocetin-8-O-β-D-gentiobioside (7) 4.0%-5.0%

13Z-crocetin-8'-O-β-D-gentiobioside (8) 8.0%-10.0% crocetin mono-β-D-glucopyranoside (9) 1.0%-3.0%.

In the above, the above each ingredient has the following structural formula respectively,

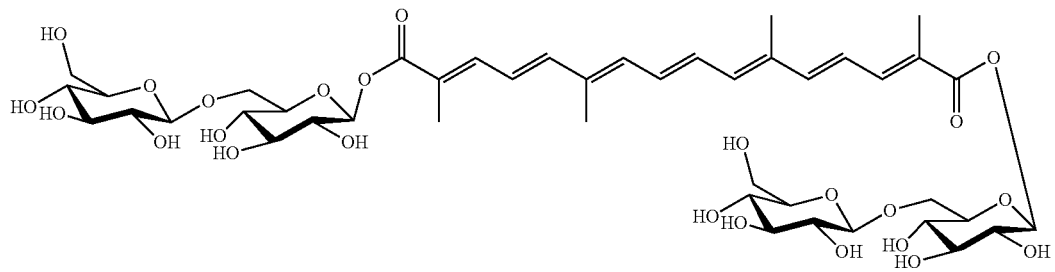

1 crocetin di-β-D-gentiobioside
(trans-crocetin di(β-D-gentiobiosyl) ester)
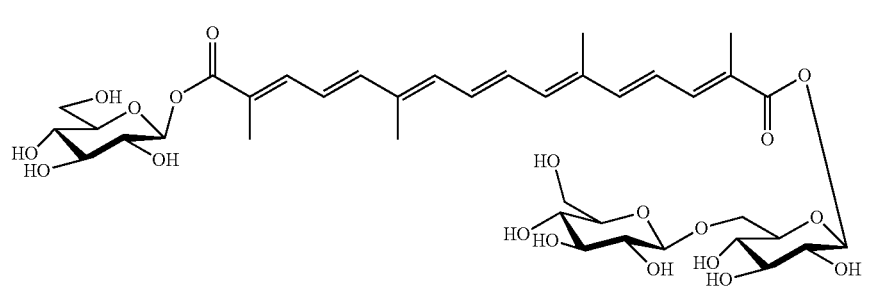
crocetin-β-D-glucopyranosyl-β-D-gentiobioside
(trans-crocetin β-D-gentiobiosyl-β-D-glucosyl ester)
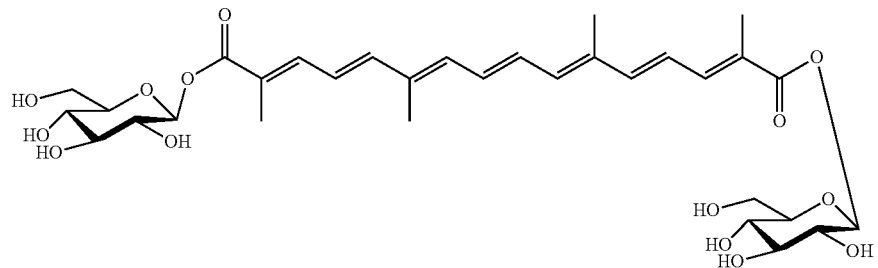
crocetin di-β-D-glucopyranoside
(trans-crocetin di(β-D-glucosyl) ester)
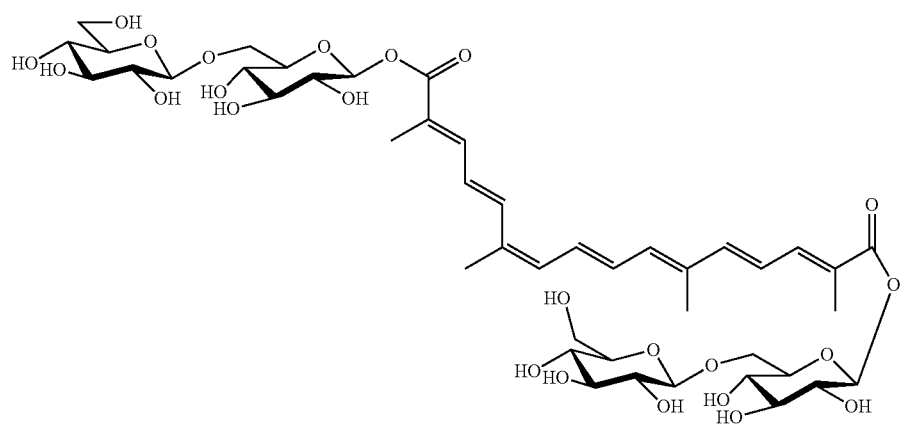

13Z-crocetin di-β-D-gentiobioside
(13-cis-crocetin di(β-D-gentiobiosyl) ester)
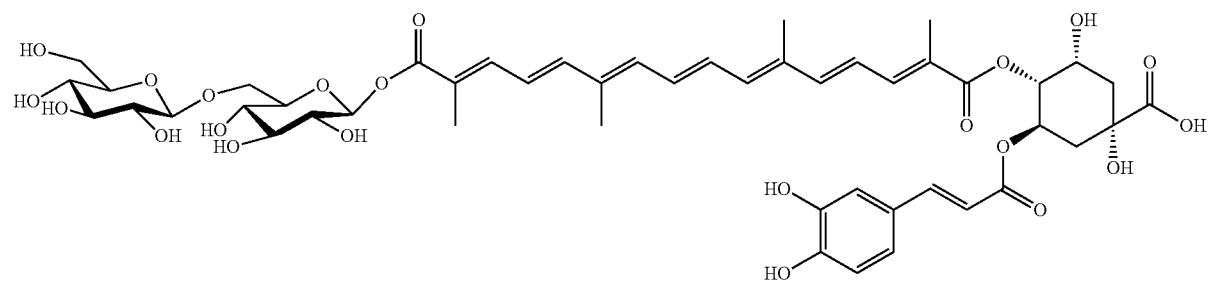
5
neocrocin B
6
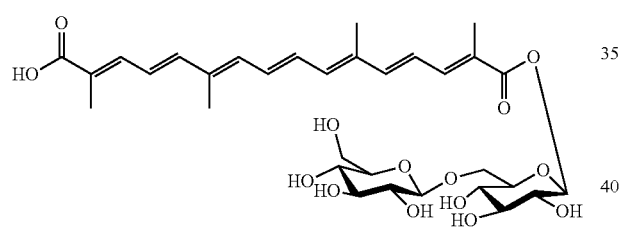
crocetin mono-β-D-gentiobioside
(trans-crocetin mono(β-D-gentiobiosyl) ester)
7
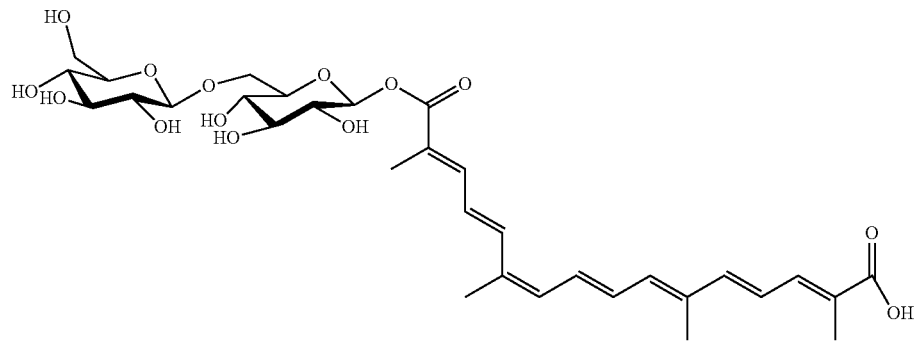

13Z-crocetin-8-O-β-D-gentiobioside
(13-cis-crocetin-8-O-β-D-gentiobiosyl ester)

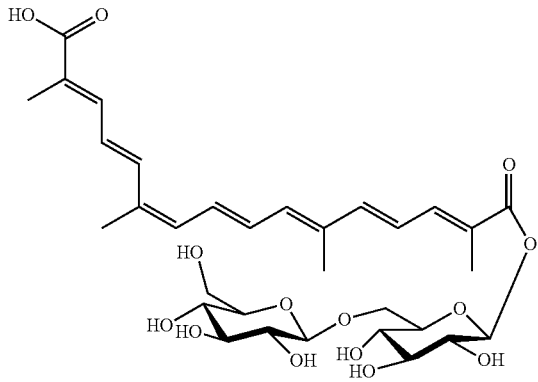

13Z-crocetin-8'-O-β-D-gentiobioside
(13-cis-crocetin κ'-O-β-D-gentiobiosyl ester)

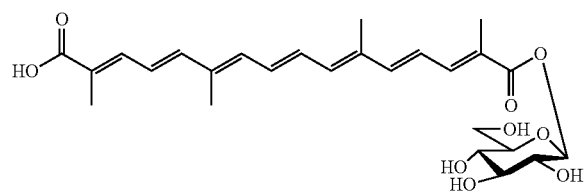

crocetin mono-β-D-glucopyranoside
(trans-crocetin mono(β-D-glucosyl) ester)

[7] A crocins active site, wherein it includes the composition according to any one of items [1]-[6].

[8] The crocins active site according to item [7], wherein the crocins active site is extracted from *Gardenia*.

[9] The crocins active site according to item [7], wherein the UPLC characteristic chromatogram of the crocins active site mainly includes 9 chromatographic peaks, the retention time of crocetin mono-β-D-gentiobioside is set as 1, and the relative retention time is obtained for the various chromatographic peaks respectively, the retention time of crocetin di-β-D-gentiobioside is 0.38±0.02, the retention time of crocetin-β-D-glucopyranosyl-β-D-gentiobioside is 0.48±0.02, the retention time of crocetin di-β-D-glucopyranoside is 0.60±0.02, the retention time of 13Z-crocetin di-β-D-gentiobioside is 0.78±0.02, the retention time of neocrocin B is 0.89±0.02, the retention time of crocetin mono-β-D-gentiobioside is 1.00, the retention time of 13Z-crocetin-8-O-β-D-gentiobioside is 1.13±0.02, the retention time of 13Z-crocetin-8'-O-β-D-gentiobioside is 1.14±0.02, and the retention time of crocetin mono-β-D-glucopyranoside is 1.19±0.02.

[10] The crocins active site according to item [9], wherein the UPLC characteristic chromatogram of the crocins active site is established by reversed-phase ultra-performance liquid chromatography under the chromatographic condition that octadecylsilane chemically bonded silica is the stationary phase, acetonitrile-water solution containing 0.1% of formic acid is the mobile phase, and gradient elution is done, the flow velocity is 0.6 mL/min, and detection wavelength is 440 nm, and the temperature of the chromatographic column is 35° C.

[11] A crocins active site, wherein the crocins active site is prepared by the following method:

(1) after pulverizing dry *Gardenia* fruit appropriately, performing hot extraction or ultrasonic extraction with ethanol, methanol or water for different times and durations, concentrating the extracting solution at reduced pressure to obtain total *Gardenia* extract;

(2) dissolving the total *Gardenia* extract in an appropriate amount of water, centrifuging it, passing the supernatant through macroporous resin open column chromatography, eluting an appropriate column volume with water and/or 30%-95% ethanol, collecting the eluent, concentrating 70% ethanol eluent at reduced pressure to obtain the crocins active site.

[12] A method of preparing the crocins active site according to any one of items [7]-[10], wherein it includes steps of:

(1) after pulverizing dry *Gardenia* fruit appropriately, performing hot extraction or ultrasonic extraction with ethanol, methanol or water for different times and durations, concentrating the extracting solution at reduced pressure to obtain total *Gardenia* extract;

(2) dissolving the total *Gardenia* extract in an appropriate amount of water, centrifuging it, passing the supernatant through macroporous resin open column chromatography, eluting an appropriate column volume with water and/or 30%-95% ethanol, collecting the eluent, concentrating at reduced pressure to obtain the crocins active site.

[13] The method according to item [12], wherein in step (1), 4 times of 60% ethanol is used and it is extracted for 3 times by heating under reflux, 2 hours each time;

in step (2), the elution is performed respectively with water, 30% ethanol, 50% ethanol, 70% ethanol and 95% ethanol, 4 column volumes are eluted at each gradient, the 70% ethanol eluent is concentrated at reduced pressure so as to obtain the crocins active site.

[14] Use of the crocins active site according to any one of items [7]-[11] in preparing drugs which improve learning and memory abilities.

[15] Use of the crocins active site according to any one of items [7]-[11] in preparing drugs which prevent and treat Alzheimer's disease.

[16] A pharmaceutical composition, wherein the pharmaceutical composition includes the crocins active site according to any one of items [7]-[11], one or more other drugs protective of central nervous system and appropriate pharmaceutical excipients.

[17] Use of the pharmaceutical composition according to item [16] in preparing drugs which prevent and treat central nervous system degenerative disorders.

Beneficial Effects (1) The composition of the present disclosure consists of several newly structured crocins compounds.

(2) The crocins active site of the present disclosure further includes 2 newly structured crocins compounds.

(3) The preparation process of the present disclosure is simple and the present disclosure uses the internationally recognized AD pharmacological evaluation model and proves the excellent effect of the crocins active site of the present disclosure in treating AD at a low dosage.

DETAILED DESCRIPTION OF EMBODIMENTS

The technical solutions of the present disclosure will be further explained with reference to examples below, but the present disclosure is not limited to these examples.

Example 1: Method of Preparing *Gardenia* Sourced Crocins Active Site 40.0 kg of dry *Gardenia* fruit was taken and pulverized appropriately, then 4 times of 60% ethanol was used for extraction for 3 times by heating under reflux, 2 hours each time. The extracting solution was combined. The solvent was evaporated at reduced pressure and 6.2 kg of total *Gardenia* extract was obtained. The extract was dissolved in an appropriate amount of water and centrifuged. Then it was subjected to macroporous resin open column chromatography (20.0×90 cm). Then it was eluted respectively with 4 times column volume of water, 30%, 50%, 70% and 95% ethanol. The eluent from respective part was collected. The solvent was recycled at reduced pressure. About 4.5 kg was obtained from the combination of water elution and 30% ethanol elution, 710.0 g from 50% ethanol elution, 150.0 g from 70% ethanol elution, 112.0 g from 95% ethanol elution. The one from 70% ethanol elution is the *Gardenia* sourced crocins active site GJ-4.

Figure 1:
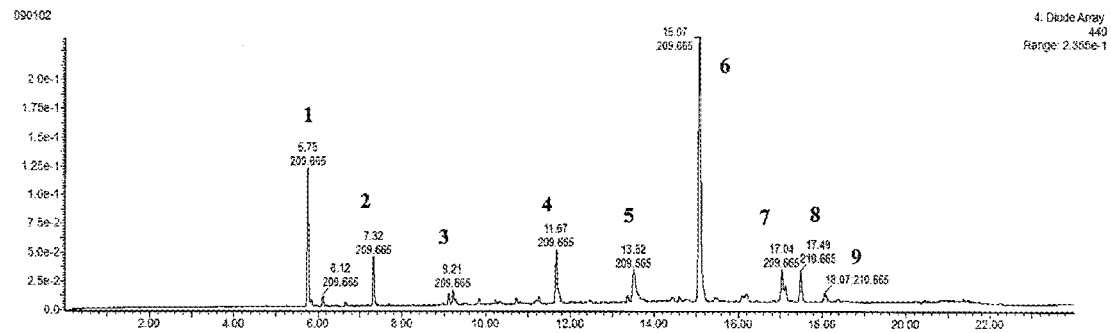
FIG. 1 is characteristic chromatogram of *Gardenia* sourced crocins active site determined by liquid phase analysis with UPLC.
Figure 2:
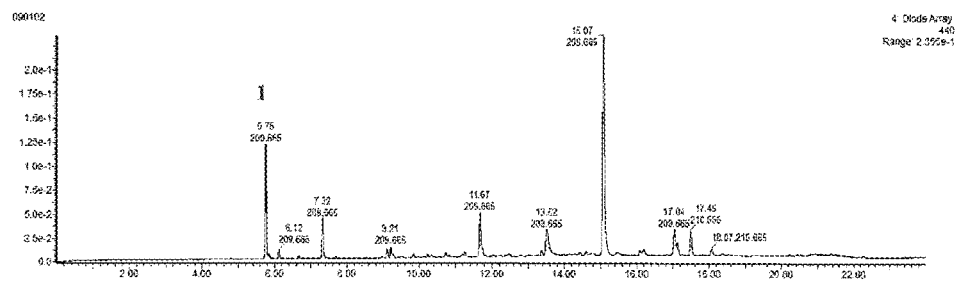
FIG. 2 is a chromatographic peak assignment chromatogram of compound 1 isolated from *Gardenia* sourced crocins active site under the same UPLC condition.
Figure 3:
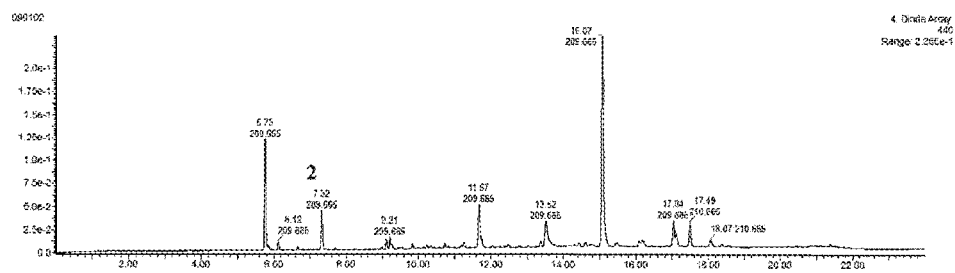
FIG. 3 is a chromatographic peak assignment chromatogram of compound 2 isolated from *Gardenia* sourced crocins active site under the same UPLC condition.
Figure 4:
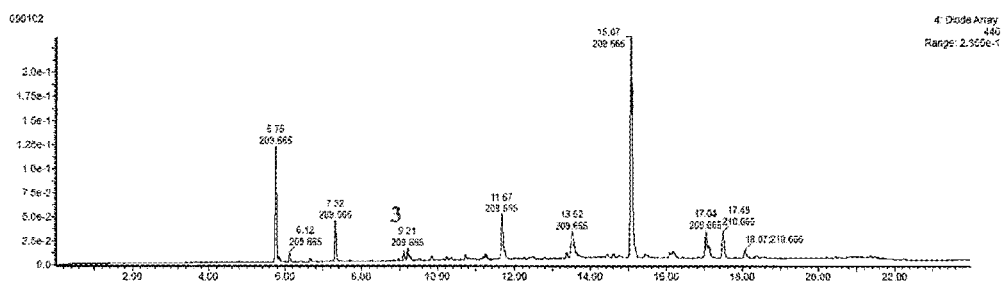
FIG. 4 is a chromatographic peak assignment chromatogram of compound 3 isolated from *Gardenia* sourced crocins active site under the same UPLC condition.
Figure 5:
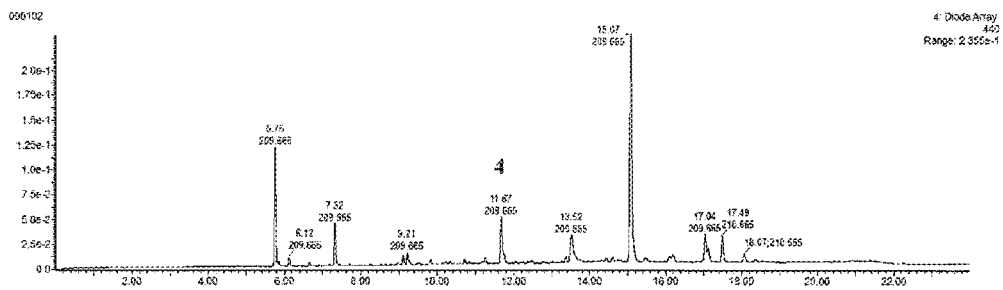
FIG. 5 is a chromatographic peak assignment chromatogram of compound 4 isolated from *Gardenia* sourced crocins active site under the same UPLC condition.
Figure 6:
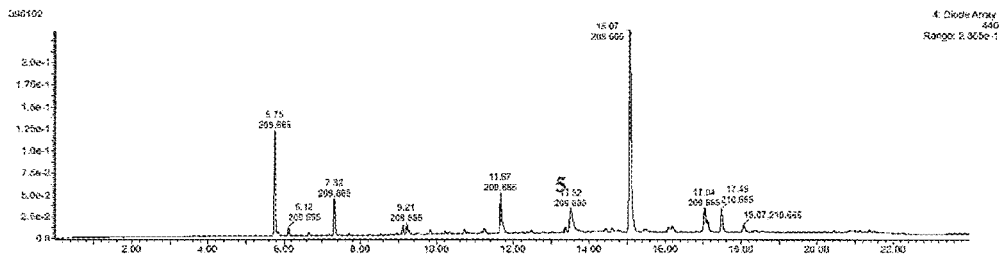
FIG. 6 is a chromatographic peak assignment chromatogram of compound 5 isolated from *Gardenia* sourced crocins active site under the same UPLC condition.
Figure 7:
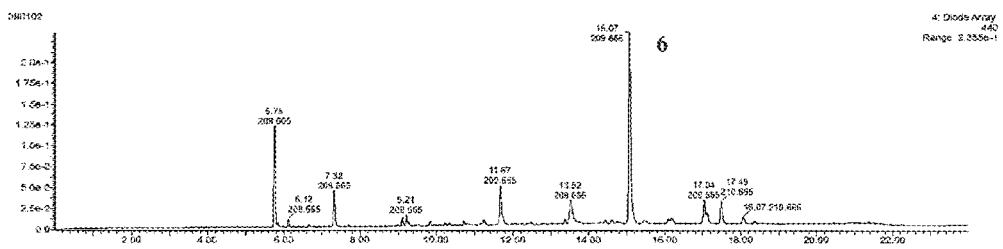
FIG. 7 is a chromatographic peak assignment chromatogram of compound 6 isolated from *Gardenia* sourced crocins active site under the same UPLC condition.
Figure 8:
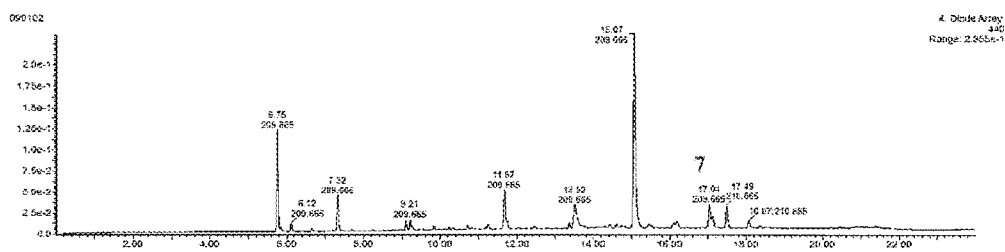
FIG. 8 is a chromatographic peak assignment chromatogram of compound 7 isolated from *Gardenia* sourced crocins active site under the same UPLC condition.
Figure 9:
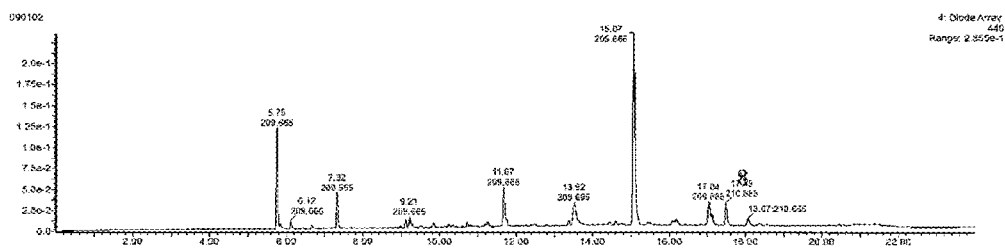
FIG. 9 is a chromatographic peak assignment chromatogram of compound 8 isolated from *Gardenia* sourced crocins active site under the same UPLC condition.
Figure 10:
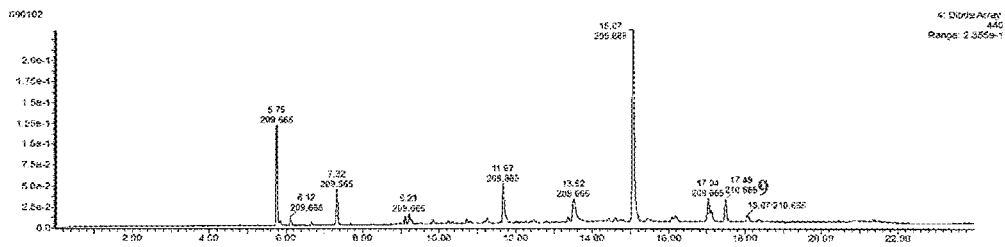
FIG. 10 is a chromatographic peak assignment chromatogram of compound 9 isolated from *Gardenia* sourced crocins active site under the same UPLC condition.

Example 2: Isolation and Identification of Main Ingredients in the *Gardenia* Sourced Crocins Active Site FIG. 1 shows the UPLC characteristic chromatogram of the *Gardenia* sourced crocins active site prepared in Example 1. With the help of the characteristic chromatogram, the structures of 9 compounds, i.e. crocetin di-β-D-gentiobioside, crocetin-β-D-glucopyranosyl-β-D-gentiobioside, crocetin di-β-D-glucopyranoside, 13Z-crocetin di-β-D-gentiobioside, neocrocin B, crocetin mono-β-D-gentiobioside, 13Z-crocetin-8-O-β-D-gentiobioside, 13Z-crocetin-8'-O-β-D-gentiobioside and crocetin mono-β-D-glucopyranoside were identified by isolation means including ODS column chromatography and RP-HPLC preparative liquid chromatograph and by analysis and identification methods including UV, MS and NMR.

The compounds as isolated were assigned under the same chromatographic conditions as the UPLC characteristic chromatogram of the *Gardenia* sourced crocins active site. See FIGS. 2-10 for the particular assignment process.

2.1 Isolation Process

The obtained *Gardenia* sourced crocins active site was isolated by column chromatography on silica gel eluted with chloroform, methanol and water at a ratio of 8:2:0.2 to give compound 6 (about 7.0 g) and eluted with chloroform, methanol and water at a ratio of 9:1:0.1 to give compound 9 (136.5 mg). It was subjected to open column chromatography on ODS eluted with 50% methanol-water to give compound 1 (545.1 mg), eluted with 55% methanol-water to give compound 2 (143.7 mg) and eluted with 50% methanol-water to give compound 3 (315.7 mg). It was isolated by preparative high performance liquid column chromatography on ODS eluted with 60% methanol-water to give compound 4 (265.7 mg, $t_R$=16.6 min), eluted with 68% methanol-acid water (0.1% $CH_3COOH$) to give compound 5 (520.9 mg, $t_R$=9.5 min), isolated with 42% acetonitrile-acid water (0.1% $CH_3COOH$) to give compound 7 (8.0 mg, $t_R$=17.9 min) and compound 8 (16.0 mg, $t_R$=21.5 min).

2.2 Structural Analysis of Compounds 2.2.1 Compound 1

Red amorphous powder. HR-ESI-MS gives m/z 999.3680 [M+Na]$^+$ (calculated value, 999.3685), formula determined as $C_{44}H_{64}O_{24}$, calculated degree of unsaturation, 13.

$^1$H-NMR (600 MHz, in DMSO-$d_6$) suggests characteristic alkenyl hydrogen signal [δ 7.35 (2H, d, J=10.8 Hz), 6.87 (2H, dd, J=7.8, 2.4 Hz), 6.82 (2H, d, J=15.0 Hz), 6.67 (2H, dd, J=15.0, 12.6 Hz), 6.53 (2H, br.d, J=9.6 Hz),]; 4 pairwise overlapping saccharide end group signals [δ 5.42 (2H, d, J=8.4 Hz), 4.17 (2H, d, J=7.8 Hz)] and 4 pairwise overlapping methyl hydrogen signals [δ 2.00 (6H, s), 1.97 (6H, s)] of crocetin.

By comparison with the documentation[11], it is determined that compound 1 is crocetin di-β-D-gentiobioside. See Table 1 for $^{13}$C-NMR of compound 1.

2.2.2 Compound 2

Red amorphous powder. HR-ESI-MS gives m/z 837.3166 [M+Na]$^+$ (calculated value, 837.3157), formula determined as $C_{38}H_{54}O_{19}$, calculated degree of unsaturation, 12.

¹H-NMR (600 MHz, in DMSO-d₆) suggests characteristic alkenyl hydrogen signal [δ 7.35 (2H, d, J=11.4 Hz), 6.86 (2H, dd, J=8.4, 3.0 Hz), 6.82 (1H, d, J=14.4 Hz), 6.81 (1H, d, J=15.0 Hz), 6.66 (2H, dd, J=15.0, 12.0 Hz), 6.54 (2H, br.d, J=8.4 Hz),], 4 methyl hydrogen signals [δ 1.99 (6H, s), 1.97 (6H, s)] and 3 saccharide end group proton signals [δ 5.42 (2H, d, J=7.8 Hz), 4.17 (1H, d, J=7.8 Hz)] of crocetin.

By comparison with the documentation[11], it is determined that compound 2 is crocetin-β-D-glucopyranosyl-β-D-gentiobioside. See Table 1 for ¹³C-NMR of compound 2.

2.2.3 Compound 3

Red amorphous powder. ESI-MS (positive) gives m/z 675 [M+Na]⁺, 1327 [2M+Na]⁺. It is speculated that its molecular weight is 652.

¹H-NMR (600 MHz, in DMSO-d₆) suggests characteristic alkenyl hydrogen signal [δ 7.35 (2H, d, J=11.4 Hz), 6.86 (2H, dd, J=8.4, 3.0 Hz), 6.81 (2H, d, J=15.0 Hz), 6.67 (2H, dd, J=15.0, 11.4 Hz), 6.54 (2H, br.d, J=9.6 Hz),]; 2 overlapping saccharide end group signals [δ 5.42 (2H, d, J=7.8 Hz)] and 4 pairwise overlapping methyl hydrogen signals [δ 2.00 (6H, s), 1.97 (6H, s)] of crocetin.

By comparison with the documentation[12], it is determined that compound 3 is crocetin di-β-D-glucopyranoside. See Table 1 for ¹³C-NMR of compound 3.

2.2.4 Compound 4

Red amorphous powder. HR-ESI-MS gives m/z 999.3665 [M+Na]⁺ (calculated value, 999.3685), formula determined as $C_{44}H_{64}O_{24}$, calculated degree of unsaturation, 13.

Compound 4 is an isomer of compound 1. By comparing their ¹H-NMR (600 MHz, in DMSO-d₆), there is a big change in the alkenyl hydrogen area of compound 4, and the rest of signals are substantially consistent with compound 1. In ¹³C-NMR (150 MHz, in DMSO-d₆) of compound 4, the configuration change in the double bond on the 13th site breaks the highly symmetric structure of the compound. Each of many overlapping alkenyl carbons signals becomes 2 signals, the methyl carbon signal on the 20th site shifts to δ 20.0 toward the low field, and the end group hydrogen signal of the saccharide connected with the carbon on the 8th site changes from 5.42 to 5.44.

By comparison with the documentation[11], it is determined that compound 4 is 13Z-crocetin di-β-D-gentiobioside. See Table 1 for ¹³C-NMR of compound 4.

2.2.5 Compound 5

Red amorphous powder. ESI-MS (positive) gives m/z 1011 [M+Na]⁺ and indicates that the molecular weight of the compound is 988. HR-ESI-MS gives 989.3642[M+H]⁺ (calculated value, 989.3654), formula determined as $C_{48}H_{60}O_{22}$, calculated degree of unsaturation, 19.

In the ¹H-NMR (600 MHz, in DMSO-d₆) chromatogram of compound 5, the low field area shows a group of trans-alkenyl hydrogen signals [δ 7.44 (1H, d, J=15.6 Hz, H-3'''), 6.16 (1H, d, J=16.2 Hz, H-2''')]; a group of inter-coupling aromatic proton signals [δ 7.03 (1H, d, J=1.8 Hz, H-5'''), 6.98 (1H, dd, J=8.4, 1.8 Hz, H-9''') 6.74 (1H, d, J=7.8 Hz, H-8''')]. In combination with ¹³C-NMR (150 MHz, in DMSO-d₆) signals, δ 148.5 (C-7'''), 145.6 (C-6'''), 125.2 (C-4'''), 121.6 (C-9'''), 115.7 (C-8''') and 114.9 (C-5'''), it indicates that there is 1,3,4-trisubstituted benzene ring in the structure. The HMBCs of the alkenyl hydrogen proton signals H-3'''/C-4''', C-5''', C-9''', C-1'''; H-2'''/C-1''', C-4''' are long-range correlated. It indicates that it contains a caffeoyl segment of $C_6$-$C_3$.

The saccharide end group proton signals [δ 5.42 (1H, d, J=7.8 Hz, H-1) and 4.17 (1H, d, J=7.8 Hz, H-1')] indicate that the two glucose residues both have a β configuration. In the HMBC chromatography, the correlated peaks H-6/C-1' and H-1'/C-6 indicate that the two glucosyl groups are in 1→6 bond and thus form a gentiobiosyl. The hydrolytic derivatization experiment of saccharide indicate that the glucose has a D configuration as its absolute configuration.

By removing 2 glucose residues and 1 caffeoyl segment of $C_6$-$C_3$ and comparing with known documentation, the characteristic crocetin signals in the structure may be assigned.

By ¹H-¹H COSY, HSQC and HMBC chromatograms, it is identified that there is structural segment of 3-caffeoylquinic acid in the structure, and it is speculated by HMBC chromatogram that the 4th site of the caffeic acid is bonded with crocetin[13].

By searching, compound 5 is a new compound that has never been reported and is named neocrocin B. See Table 1 for ¹³C-NMR of compound 5.

2.2.6 Compound 6

Red amorphous powder. HR-ESI-MS gives [M+Na]⁺ of 675.2625 (calculated value, 675.2629), formula determined as $C_{32}H_{44}O_{14}$, calculated degree of unsaturation, 11.

¹H-NMR (600 MHz, in DMSO-d₆) suggests characteristic alkenyl hydrogen signal, 2 saccharide end group signals and 4 methyl hydrogen signals of crocetin.

By comparison with the documentation[14], it is determined that compound 6 is crocetin mono-β-D-gentiobioside. See Table 1 for ¹³C-NMR of compound 6.

2.2.7 Compound 7

Red amorphous powder. ESI-MS (positive) gives m/z 675 [M+Na]⁺, m/z 1327 [2M+Na]⁺ and indicates that the molecular weight is 652. HR-ESI-MS gives [M+Na]⁺ of 675.2617 (calculated value, 675.2629), formula determined as $C_{32}H_{44}O_{14}$, calculated degree of unsaturation, 11.

Compound 7 is a cis geometrical isomer of compound 6. But the difference lies in that compound 6 has two types of cis geometrical isomers as the compound 6 itself has an asymmetric structure. By ¹H, ¹³C-NMR and two-dimensional nuclear magnetic data analysis, it is determined that compound 7 is 13Z-crocetin-8-O-β-D-gentiobioside. See Table 1 for ¹³C-NMR of compound 7.

2.2.8 Compound 8

Red amorphous powder. ESI-MS (positive) gives m/z 675 [M+Na]⁺, m/z 1327 [2M+Na]⁺ and indicates that the molecular weight is 652. HR-ESI-MS gives [M+Na⁺] of 675.2617 (calculated value, 675.2629), formula determined as $C_{32}H_{44}O_{14}$, calculated degree of unsaturation, 11.

Compound 8 is another geometrical isomer of compound 6. By one-dimensional and two-dimensional nuclear magnetic data analysis, compound 8 is identified as 13Z-crocetin-8'-O-β-D-gentiobioside. By searching, compound 8 is a new compound that has never been reported. See Table 1 for its ¹³C-NMR.

2.2.9 Compound 9

Red amorphous powder. HR-ESI-MS gives 513.2095 [M+Na]⁺ (calculated value, 513.2101), 1003.4303 [2M+Na]⁺, formula determined as $C_{26}H_{34}O_9$, calculated degree of unsaturation, 10.

$^1$H-NMR (600 MHz, in DMSO-$d_6$) suggests characteristic alkenyl hydrogen signal, 1 saccharide end group signal and 4 methyl hydrogen signals of crocetin.

By comparison with the documentation[11], it is determined that compound 9 is crocetin mono-β-D-glucopyranoside. See Table 1 for $^{13}$C-NMR of compound 9.

2.3 UPLC-Q/TOF-MS Analysis of *Gardenia* Sourced Crocins Active Site

2.3.1 Chromatographic Condition

BEH C18 (3.0 mm×150 mm, 1.7 μm); mobile phase: solvent A (water, 0.1% formic acid) and solvent B (acetonitrile, 0.1% formic acid), gradient elution (0 min-20% B, 0.5 min-20% B, 19 min-50% B, 20 min-100% B, 23 min-100% B, 24 min-20% B), flow rate: 0.6 mL/min, column temperature: 35° C., detection wavelength: 440 nm.

2.3.2 Mass Spectrum Condition

Positive ion mode of electrospray, capillary voltage: 2.0 kV; solvent-removing stream: N$_2$, flow rate 600 L/h, solvent-removing temperature 300° C.; taper hole stream: N$_2$, flow rate 50 L/h; ion source temperature: 100° C.; Extractor: 4.00 V; colliding gas:argon. See Table 2 for the mass spectrometry of 9 main chromatographic peaks.

TABLE 1

| NO. Pos. | 1 | 2 | 3 | 4 | 5 | 6 | 7 | 8 | 9 |
|---|---|---|---|---|---|---|---|---|---|
| 8, 8' | 166.2 | 166.3 | 166.2 | 166.2 | 166.2 | 166.2 | 166.1 | 169.3 | 166.2 |
|  |  |  |  |  | 167.0 | 169.2 | 169.2 | 166.2 | 169.1 |
| 9, 9' | 125.3 | 125.3$^a$ | 125.4 | 125.9 | 125.4 | 125.2 | 125.8 | 128.1 | 125.3 |
|  |  | 125.4$^a$ |  | 125.5 | 126.1 | 127.1 | 127.2 | 125.0 | 127.0 |
| 10, 10' | 139.9 | 140.0$^a$ | 139.8 | 140.1 | 140.0 | 139.9 | 140.1 | 137.9 | 139.8 |
|  |  | 139.9$^a$ |  | 140.0 | 139.0 | 138.0 | 137.9 | 140.0 | 138.0 |
| 11, 11' | 123.9 | 124.0 | 123.9 | 125.1 | 123.9$^a$ | 123.8 | 124.9 | 125.5 | 123.8 |
|  |  |  |  | 123.7 | 124.0$^a$ | 124.3 | 124.0 | 123.5 | 124.3 |
| 12, 12' | 144.6 | 144.7$^a$ | 144.5 | 136.8 | 144.7 | 144.7 | 136.8 | 135.3 | 144.6 |
|  |  | 144.6$^a$ |  | 144.7 | 144.0 | 143.3 | 143.2 | 144.7 | 143.3 |
| 13, 13' | 136.9 | 137.0 | 136.9 | 136.5 | 136.9$^a$ | 137.0 | 134.8 | 135.2 | 137.0 |
|  |  |  |  | 135.2 | 136.8$^a$ | 136.7 | 136.4 | 136.2 | 136.7 |
| 14, 14' | 136.0 | 136.1 | 136.0 | 134.6 | 136.1 | 136.0 | 134.5 | 133.7 | 136.0 |
|  |  |  |  | 135.9 | 135.7 | 135.3 | 135.1 | 135.9 | 135.3 |
| 15, 15' | 132.0 | 132.1 | 132.0 | 130.8 | 132.1 | 132.1 | 130.6 | 131.1 | 132.1 |
|  |  |  |  | 131.1 | 131.9 | 131.6 | 130.8 | 130.3 | 131.6 |
| 19, 19' | 12.7 | 12.7 | 12.7 | 12.7 | 12.7 | 12.7 | 12.7 | 12.8 | 12.7 |
|  |  |  |  |  | 12.8 | 12.8 | 12.8 | 12.7 | 12.8 |
| 20, 20' | 12.6 | 12.6 | 12.6 | 20.0 | 12.6 | 12.6 | 20.0 | 20.1 | 12.6 |
|  |  |  |  | 12.5 | 12.6 | 12.5 | 12.5 | 12.5 | 12.5 |
| 1 | 94.5 | 94.6 | 94.6 | 94.5 | 94.5 | 94.5 | 94.6 | 94.5 | 94.6 |
| 2 | 72.5 | 72.6$^a$ | 72.5 | 72.5 | 72.5 | 72.5 | 72.5 | 72.4 | 72.5 |
| 3 | 76.3 | 76.3 | 76.4 | 76.3 | 76.3 | 76.3 | 76.2 | 76.2 | 76.5 |
| 4 | 69.2 | 69.3 | 69.5 | 69.2 | 69.2 | 69.2 | 69.2 | 69.2 | 69.5 |
| 5 | 76.3 | 76.3 | 77.8 | 76.3 | 76.3 | 76.3 | 76.3 | 76.3 | 77.9 |
| 6 | 67.9 | 68.0 | 60.5 | 67.9 | 67.9 | 67.9 | 67.9 | 67.9 | 60.6 |
| 1' | 103.1 | 103.1 |  | 103.1 | 103.1 | 103.1 | 103.1 | 103.1 |  |
| 2' | 73.5 | 73.5 |  | 73.5 | 73.5 | 73.5 | 73.4 | 73.5 |  |
| 3' | 76.8 | 76.8 |  | 76.8 | 76.8 | 76.8 | 76.8 | 76.8 |  |
| 4' | 70.0 | 70.0 |  | 70.0 | 70.0 | 70.0 | 70.0 | 70.0 |  |
| 5' | 76.9 | 76.9 |  | 76.9 | 76.9 | 76.9 | 76.9 | 76.9 |  |
| 6' | 61.0 | 61.0 |  | 61.0 | 61.0 | 61.0 | 61.0 | 61.0 |  |
| 1" |  | 94.6 |  |  | 73.6 |  |  |  |  |
| 2" |  | 72.5$^a$ |  |  | 37.4 |  |  |  |  |
| 3" |  | 76.5 |  |  | 67.5 |  |  |  |  |
| 4" |  | 69.6 |  |  | 74.2 |  |  |  |  |
| 5" |  | 77.9 |  |  | 66.3 |  |  |  |  |
| 6" |  | 60.6 |  |  | 37.6 |  |  |  |  |
| 7" |  |  |  |  | 174.8 |  |  |  |  |
| 1''' |  |  |  |  | 165.6 |  |  |  |  |
| 2''' |  |  |  |  | 113.6 |  |  |  |  |
| 3''' |  |  |  |  | 145.6 |  |  |  |  |
| 4''' |  |  |  |  | 125.2 |  |  |  |  |
| 5''' |  |  |  |  | 114.9 |  |  |  |  |
| 6''' |  |  |  |  | 145.6 |  |  |  |  |
| 7''' |  |  |  |  | 148.5 |  |  |  |  |
| 8''' |  |  |  |  | 115.7 |  |  |  |  |
| 9''' |  |  |  |  | 121.6 |  |  |  |  |

$^a$means signals could be interchangeable with the corresponding position in one compound.

TABLE 2

| NO. | $t_R$ | Selected Ion | Measured mass | Calculated mass | Mass error (ppm) | Elemental composition | Fragmentation | Identification |
|---|---|---|---|---|---|---|---|---|
| 1* | 5.79 | $[M + Na]^+$ | 999.3676 | 999.3685 | −0.9 | $C_{44}H_{64}O_{24}$ | 976.3770, 999.3676; 652.2716, 675.2599; 329.1764, 311.1641, 293.1528 | crocetin di-β-D-gentiobioside |
| 2* | 7.35 | $[M + Na]^+$ | 837.3118 | 837.3157 | −4.7 | $C_{38}H_{54}O_{19}$ | 814.3245, 837.3118; 675.2667; 329.1737, 311.1633, 293.1537 | crocetin-β-D-glucopyranosyl-β-D-gentiobioside |
| 3* | 9.15 | $[M + Na]^+$ | 675.2614 | 675.2629 | −2.2 | $C_{32}H_{44}O_{14}$ | 652.2706, 675.2614; 513.2049; 329.1725, 311.1632, 293.1535 | crocetin di-β-D-glucopyranoside |
| 4* | 11.71 | $[M + Na]^+$ | 999.3680 | 999.3685 | −0.5 | $C_{44}H_{64}O_{24}$ | 976.3772, 999.3680, 1953.7651; 652.2731; 329.1740, 311.1644, 293.1530 | 13Z-crocetin di-β-D-gentiobioside |
| 5* | 13.56 | $[M + H]^+$ | 989.3597 | 989.3654 | −5.8 | $C_{48}H_{60}O_{22}$ | 988.3539, 989.3597, 1976.7084; 665.2532; 827.3113 | neocrocin B |
| 6* | 15.09 | $[M + Na]^+$ | 675.2620 | 675.2629 | −1.3 | $C_{32}H_{44}O_{14}$ | 652.2720, 675.2620; 329.1744, 311.1635, 293.1530 | crocetin mono-β-D-gentiobioside |
| 7* | 17.08 | $[M + Na]^+$ | 675.2632 | 675.2629 | 0.4 | $C_{32}H_{44}O_{14}$ | 652.2731, 675.2632; 329.1759, 311.1651, 293.1541 | 13Z-crocetin-8-O-β-D-gentiobioside |
| 8* | 17.51 | $[M + Na]^+$ | 675.2625 | 675.2629 | −0.6 | $C_{32}H_{44}O_{14}$ | 652.2675, 675.2625; 329.1741, 311.1641, 293.1539 | 13Z-crocetin-8'-O-β-D-gentiobioside |
| 9* | 18.03 | $[M + Na]^+$ | 513.2098 | 513.2101 | −0.6 | $C_{26}H_{34}O_9$ | 490.2192, 513.2098, 1003.4275; 329.1747, 311.1643, 293.1534 | crocetin mono-β-D-glucopyranoside |

*indicates the comparison with control products (which are monomeric compounds obtained by isolation)

Example 3: *Gardenia* Sourced Crocins Active Site GJ-4 Improves Learning and Memory Impairment in Mice Induced by Scopolamine (Step-Down Test)

3.1 Principle of the Step-Down Test

The device used in the step-down test was a rectangular reflection box with a size of 10 cm×10 cm×60 cm. The reflection box was partitioned into 5 compartments by black plastic plates and provided with copper grid on its floor at an interval of 0.5 cm. The grid could be energized. The voltage strength was controlled by a transformer. A wooden platform with a height and a diameter both being 4.5 cm was provided at the right corner in each compartment. During the time of test, 36 V alternating current was supplied. When shocked, the mice normally responded by jumping onto the safe platform to avoid the harmful stimulus. No power was supplied on the first day. Mice were put in the reflection box and were free for 5 min to get familiar with the environment. 24 h later, the copper grid was energized (with 36 V alternating current). The timings when the respective groups of mice first jumped onto the safe platform after being shocked (response time) and error times that they jumped from the safe platform within 5 min (basic error times) were recorded as the learning test scores. The next day, the above process was repeated. The timings when the respective groups of mice first jumped from the safe platform (latent period) and times of being shocked within 5 min (error times) were recorded as the memory test scores. In test, if the mice stayed on the safe platform for more than 5 min, the latent period was taken as 5 min.

3.2 Scheme of Step-Down Test

Figure 11:
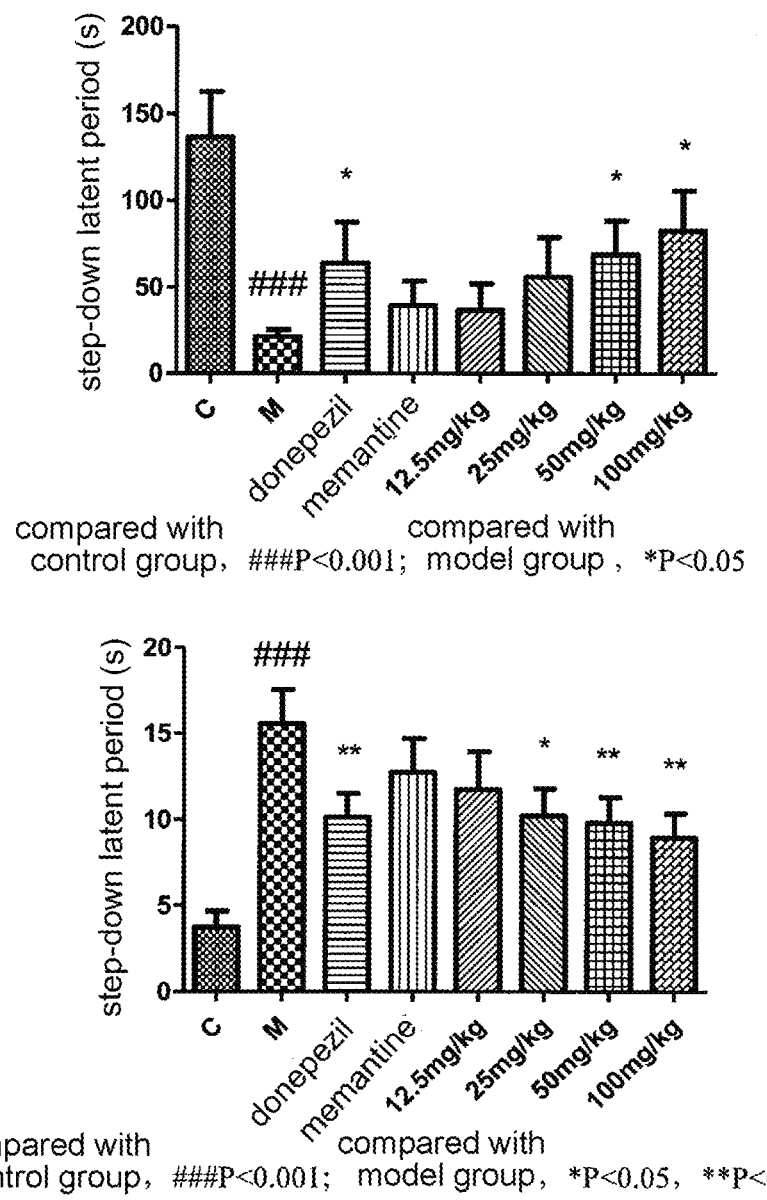
FIG. 11 is a diagram showing the protective effect of *Gardenia* sourced crocins active site GJ-4 on learning and memory impairment in mice caused by scopolamine.

ICR mice, male, 160 mice, divided into 8 groups, 20 in each group, respectively control group, model group, donepezil (5 mg/kg) group, memantine (5 mg/kg) group, GJ-4 (12.5 mg/kg) group, GJ-4 (25 mg/kg) group, GJ-4 (50 mg/kg) group and GJ-4 (100 mg/kg) group. The mice were administrated for 7 consecutive days in advance. Then the mice were trained in step-down test on day 5 and day 6. On day 7, after 1 h of administration, the model group and the administrated groups were administrated with scopolamine (2 mg/kg) by intraperitoneal injection respectively. 30 min later, they were put in behavior test by step-down method. The timing when the mice first jumped down (latent period) and times of jumping down within 5 min (error times) were recorded. See FIG. 11 for the data.

The test result shows that *Gardenia* sourced crocins active site GJ-4 shows a good improvement effect in animal dementia induced by scopolamine. GJ-4 can obviously elongate the step-down latent period for mice and reduce the step-down error times. 25 mg/kg, 50 mg/kg and 100 mg/kg dosage groups exhibit a certain dose-effect relationship. Medium and high dosage groups have an equivalent efficacy with the positive control drug, donepezil. And the test result is reproducible. No toxic reaction associated with administration was observed in any dosage groups in the test.

Example 4: *Gardenia* Sourced Crocins Active Site GJ-4 Improves Learning and Memory Impairment in Mice Induced by Intracerebroventricular $A\beta_{25-35}$ Injection (Step-Down Test and Morris Water Maze Test)

4.1 Intracerebroventricular Injection Operation for Mice, Grouping and Administration 5 μg/μL $A\beta_{25-35}$ was prepared with sterile triple distilled water and placed in an incubator at 37° C. and left to stand for 7 days to aggregate. Then it was cryopreserved in a refrigerator at −20° C. After being adaptively fed for two days, ICR mice were anesthetized with 4% chloral hydrate (10 mg/kg) by intraperitoneal injection. Then they were fixed on a stereotaxic apparatus. The head skin of the mice was cut open along the center line with surgical scissors to expose the bregma and the lambdoidal suture. The skull was drilled with an electric drill at the left paracele at a spot 2 mm behind the bregma, 2 mm to the left of the center line, and 1.7 mm under the cerebral dura mater to an extent that the meninx would not be damaged, and then 2 μL $A\beta_{25-35}$ was injected to the left paracele of the mice, 10 μg/mouse. The administration was done within 1 min. The injection needle was left there for 3 min and then pulled out slowly. Then the incision was sutured with surgical suture. The mice were administrated with ampicillin (5 mg/kg) by intramuscular injection and then put into a cage. For the sham group, the mice were injected with 2 μL sterile triple distilled water in the left paracele at a spot 2 mm behind the bregma, 2 mm to the left of the center line, and 1.7 mm under the cerebral dura mater. After operation, the mice injected with $A\beta_{25-35}$ in the paracele were randomly divided into a model group, GJ-4 (25 mg/kg) group, GJ-4 (50 mg/kg) group, GJ-4 (100 mg/kg) and donepezil (5 mg/kg) group, 15 mice in each group. After operation, the mice were allowed to rest for 3 days. Each group was intragastrically administrated with drugs of corresponding dosage. The sham group and the model group were administrated with the same dosage of saline, once a day, for 12 consecutive days.

4.2 Behavior Test

4.2.1 Step-Down Test

Figure 12:
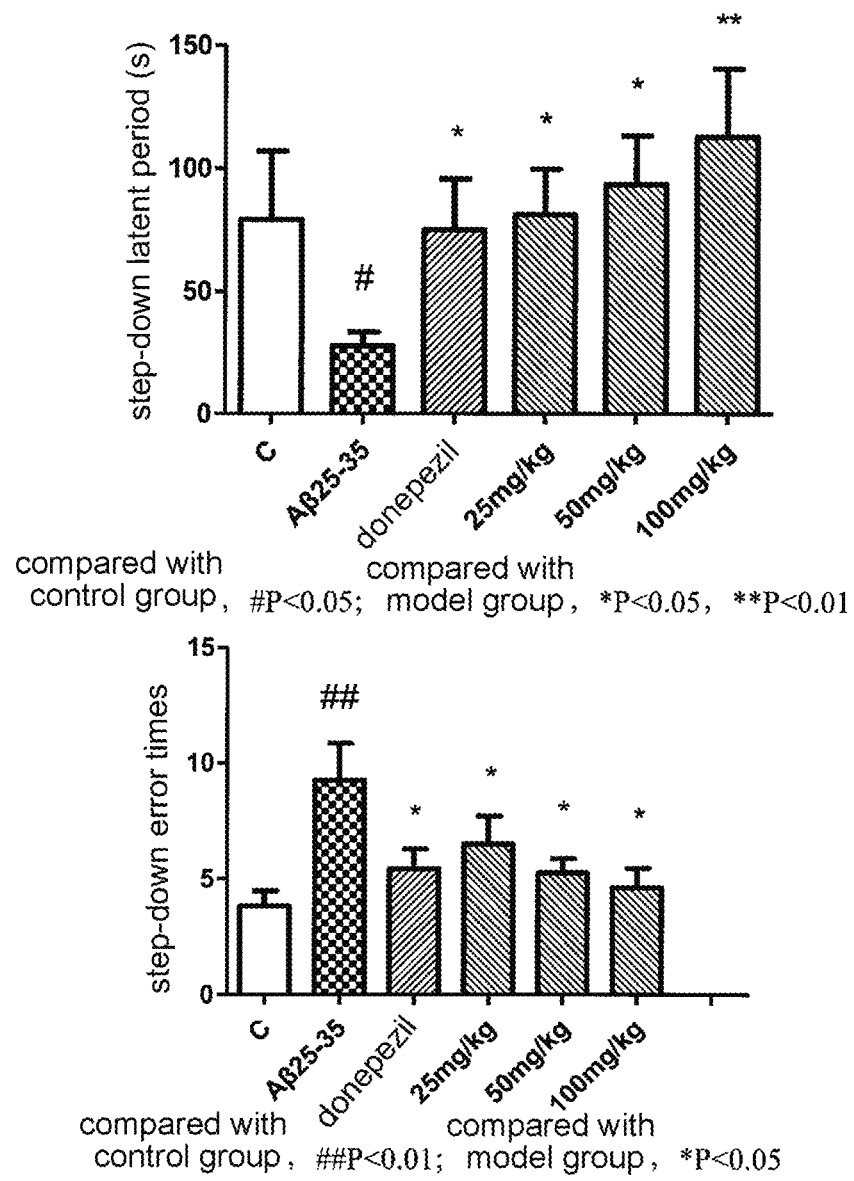
FIG. 12 is a diagram showing the protective effect of *Gardenia* sourced crocins active site GJ-4 on learning and memory impairment in mice caused by intracerebroventricular A$\beta_{25-35}$ injection (step-down test).

On day 7 after administration, the mice were tested for learning and memory abilities by step-down test. The device used in the step-down test is a rectangular reflection box with a size of 10 cm×10 cm×60 cm. The reflection box is partitioned into 5 compartments with black plastic plates and provided with copper grid on its floor at an interval of 0.5 cm. The grid can be energized. The voltage strength is controlled by a transformer. A wooden platform with a height and a diameter both being 4.5 cm is provided at the right corner in each compartment. During the time of test, 36 V alternating current is supplied. When shocked, the mice normally respond by jumping onto the safe platform to avoid the harmful stimulus. No power was supplied on the day 5 after administration. Mice were put into the reflection box and were free for 5 min to get familiar with the environment. 24$h$ later, the copper grid was energized (with 36 V alternating current). The timings when the respective groups of mice first jumped onto the safe platform after being shocked (response time) and error times that they jumped from the safe platform within 5 min (basic error times) were recorded as the learning test scores. On day 7 after administration, the above process was repeated. The timings when the respective groups of mice first jumped from the safe platform (latent period) and times of being shocked within 5 min (error times) were recorded as the memory test scores. In test, if the mice stayed on the safe platform for more than 5 min, the latent period was taken as 5 min. See FIG. 12 for the result.

4.2.2 Morris Water Maze Test

Figure 13:
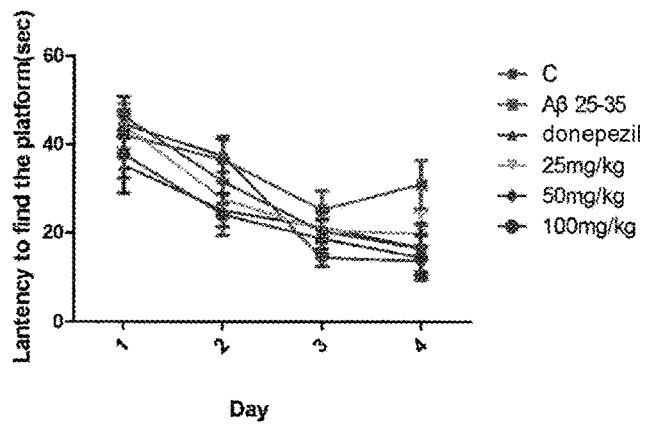
FIG. 13 is a diagram showing the protective effect of *Gardenia* sourced crocins active site GJ-4 on learning and memory impairment in mice caused by intracerebroventricular A$\beta_{25-35}$ injection (Morris water maze).
Figure 13:
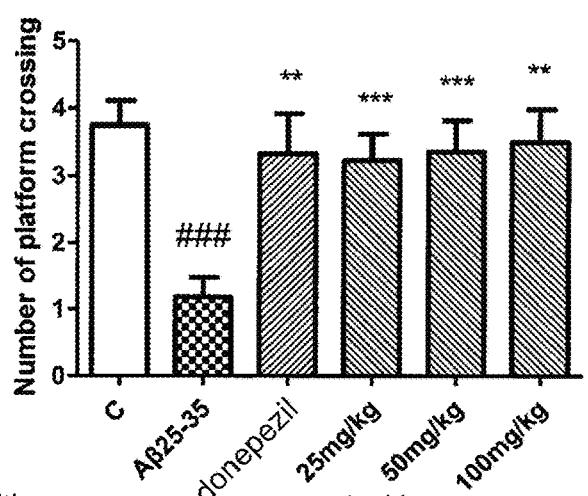
Figure 13:
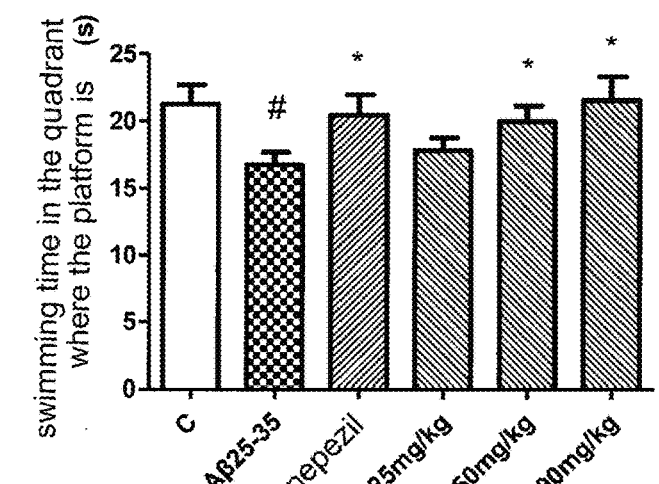

On the second day after the step-down test (i.e. day 8 after administration), the mice were further tested for learning and memory abilities by Morris water maze test (the mice in the respective groups were tested for learning and memory abilities in spatial sense of position and sense of direction). The device used in Morris water maze test was a circular pool with a diameter of 120 cm and a depth of 40 cm, provided with a layer of black adhesive tape on its internal surface. The water temperature was kept at 23-25° C. The indoor temperature was kept at 26-28° C. The water tank was randomly divided into four quadrants. The platform stayed where it was during the time of test, i.e. in the center of the second quadrant, 1-2 cm lower than the water surface. Obvious marks were made on the walls in the room for the mice to identify directions. All the objects in the room were stationary during the test, so as not to interfere with the mice. The test lasted for 5 days, twice a day. For the first 4 days, place navigation test was conducted. The mice were gently put into the water from two quadrants in sequence, facing the pool walls, in a way to avoid stress and putting the head of the mice into water. In the meantime, the latent period within which the mice found the safe platform within 1 min was recorded. The mice were allowed to stay on the safe platform for 30 s and then taken out and put back into the cage. If the mice did not find the safe platform within 1 min, they were put on the safe platform and allowed to stay for 30 s. And the latent period was taken as 60 s. The average value of latent period within which the mice found the safe platform twice a day would be the swimming result of the mice on that day. Statistical analysis was conducted. See FIG. 13 for the results. On day 5, spatial probe test was conducted. The safe platform was removed. Mice were put into the water from a selected quadrant, with their heads facing the pool walls. The times that the mice crossed the position where the platform was within 1 min and the swimming time in the quadrant where the platform was were recorded. Statistical analysis was conducted. See FIG. 13.

In the step-down test, *Gardenia* sourced crocins active site GJ-4 could obviously elongate the step-down latent period for mice and reduce the step-down error times. In the water maze test, GJ-4 obviously shortened the latent period within which the mice find the platform, increased times of crossing the platform and elongated the swimming time in the quadrant where the platform was in the meanwhile. The test result shows that GJ-4 shows a good improvement effect in learning and memory disorder in mice. Various dosage groups exhibit a certain dose-effect relationship. The high dosage groups have an equivalent or even better efficacy than the positive control drug, donepezil. No toxic reaction associated with administration was observed in any dosage groups in the test.

Example 5: Neuroprotection Effect of Crocin Monomer in *Gardenia* in SH-SY5Y Cell Damage Model Induced by L-Glutamic Acid

5.1 Culture Method of SH-SY5Y Nerve Cells

SH-SY5Y nerve cells were cultured in DMEM medium (containing 5% fetal calf serum by volume fraction) which were placed in an incubator containing 5% $CO_2$ under 37° C. They were subcultured once every 3-4 days. Cells in logarithmic phase were used for test

5.2 Screening Method of L-Glutamic Acid Damage Model

SH-SY5Y cells were inoculated in a 96-well plate at a concentration of $5\times10^3$ and continued to culture for 24 h. 100 μL chemical liquid medium containing L-glutamic acid was added to the 96-well plate so that the L-glutamic acid had a final concentration of 160 mM, the drug had a final concentrations of 10 μM, 1 μM and 0.1 μM. 3 parallel wells were arranged for each concentration. They were continued to culture for 24 h. 24 h later, the supernatant was pipetted out and discarded. 100 μL MTT (0.5 mg/mL) was added into each well. They were further incubated for 4 h. Then the supernatant was pipetted out and discarded. 150 μL DMSO was added into each well. They were vibrated for 10 min. A wavelength of 570 nm was selected. The absorbance value was measured on a microplate reader[13]. (effective rate %=$(OD_{drug}-OD_{model})/(OD_{control}-OD_{model})*100$). See Table 3 for the results.

TABLE 3

| Compound | Drug concentration (moL/L) | Viability of cells with drug |
|---|---|---|
| neocrocin B (5) | $10^{-5}$ | 40.03 ± 3.91** |
|  | $10^{-6}$ | 27.63 ± 5.36* |
|  | $10^{-7}$ | 9.89 ± 2.93 |
| crocetin mono-β-D-glucopyranoside (9) | $10^{-5}$ | 0.00 ± 0.00 |
|  | $10^{-6}$ | 0.00 ± 0.00 |
|  | $10^{-7}$ | 0.00 ± 0.00 |
| crocetin di-β-D-glucopyranoside (3) | $10^{-5}$ | 0.00 ± 0.00 |
|  | $10^{-6}$ | 0.00 ± 0.00 |
|  | $10^{-7}$ | 0.00 ± 0.00 |
| crocetin-β-D-glucopyranosyl-β-D-gentiobioside (2) | $10^{-5}$ | 0.00 ± 0.00 |
|  | $10^{-6}$ | 0.00 ± 0.00 |
|  | $10^{-7}$ | 0.00 ± 0.00 |

*P < 0.1,
**P < 0.05,
***P < 0.01.

The invention claimed is:

1. A method of improving a subject's learning and memory ability, which comprises administering to the subject who is in need thereof a composition comprising therapeutically effective amounts of crocetin mono-β-D-gentiobioside, crocetin di-β-D-gentiobioside and neocrocin B, wherein said neocrocin B has the following structural formula

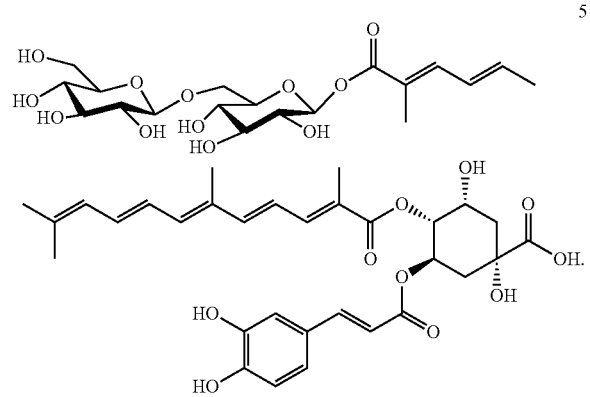

2. A method of improving a subject's learning and memory ability, which comprises administering to the subject who is in need thereof a composition comprising a therapeutically effective amount of a crocins active site extracted from *Gardenia jasminoides* Ellis, wherein the crocins active site comprises crocetin mono-β-D-gentiobioside, crocetin di-β-D-gentiobioside and neocrocin B, wherein said neocrocin B has the following structural formula

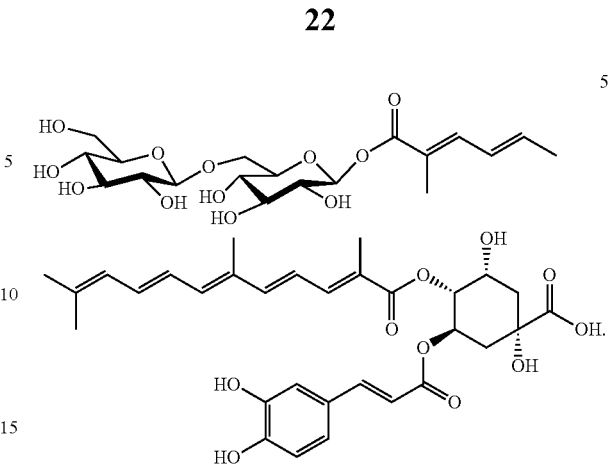

3. The method according to claim 2, wherein an ultra-performance liquid chromatography (UPLC) characteristic chromatogram of the crocins active site comprises 9 chromatographic peaks, wherein the nine chromatographic peaks comprise peaks for crocetin mono-β-D-gentiobioside, crocetin di-β-D-gentiobioside, crocetin-β-D-glucopyranosyl-β-D-gentiobioside, crocetin di-β-D-glucopyranoside, 13Z-crocetin di-β-D-gentiobioside, neocrocin B, 13Z-crocetin-8-O-β-D-gentiobioside, 13Z-crocetin-8-O-β-D-gentiobioside and crocetin mono-β-D-glucopyranoside, wherein a retention time of crocetin mono-β-D-gentiobioside is set as 1, wherein values of relative retention time are obtained for the various other chromatographic peaks respectively, and wherein the retention time of crocetin di-β-D-gentiobioside is 0.38±0.02, the retention time of crocetin-β-D-glucopyranosyl-β-D-gentiobioside is 0.48±0.02, the retention time of crocetin di-β-D-glucopyranoside is 0.60±0.02, the retention time of 13Z-crocetin di-β-D-gentiobioside is 0.78±0.02, the retention time of neocrocin B is 0.89±0.02, the retention time of crocetin mono-β-D-gentiobioside is 1.00, the retention time of 13Z-crocetin-8-O-β-D-gentiobioside is 1.13±0.02, the retention time of 13Z-crocetin-8-O-β-D-gentiobioside is 1.14±0.02, and the retention time of crocetin mono-β-D-glucopyranoside is 1.19±0.02.

4. The method according to claim 3, wherein the UPLC characteristic chromatogram of the crocins active site is established by reverse-phase ultra-performance liquid chromatography under a chromatographic condition in which octadecylsilane chemically bonded silica is a stationary phase, an acetonitrile-water solution containing 0.1% of formic acid is a mobile phase, and gradient elution is performed, wherein a flow velocity is 0.6 mL/min, a detection wavelength is 440 nm, and a temperature of a chromatographic column is 35° C.

* * * * *